United States Patent
Wells-Roth

Patent Number: 6,132,443
Date of Patent: *Oct. 17, 2000

[54] DEVICE AND METHOD FOR THE SURGICAL ANASTOMOSIS OF TUBULAR STRUCTURES

[75] Inventor: David Wells-Roth, Washington, D.C.

[73] Assignee: Surgical Innovations LLC, Potomac, Md.

[ * ] Notice: This patent is subject to a terminal disclaimer.

[21] Appl. No.: 09/324,671

[22] Filed: Jun. 3, 1999

[51] Int. Cl.⁷ ................................................ A61B 17/08
[52] U.S. Cl. .......................................... 606/155; 606/153
[58] Field of Search .................................. 606/153, 154, 606/155, 1, 142, 143, 144, 148, 233; 604/104; 128/325, 899

[56] References Cited

U.S. PATENT DOCUMENTS

| | | | |
|---|---|---|---|
| 5,037,428 | 8/1991 | Picha et al. | 606/155 |
| 5,180,392 | 1/1993 | Skeie et al. | 606/155 |
| 5,554,162 | 9/1996 | DeLange | 606/153 |
| 5,868,765 | 2/1999 | Wells-Roth | 606/153 |
| 5,893,886 | 4/1999 | Zegdi et al. | 606/153 |

Primary Examiner—Michael Buiz
Assistant Examiner—Jonathan D. Goldberg
Attorney, Agent, or Firm—Morse, Altman & Martin

[57] ABSTRACT

A device for assisting in anastomosis of tubular structures. The basic device has a generally cylindrical shape with a pair of insertion arms connected by a bridge and two or more depressions that provide space for the needle to move through within the tubular structures. The device aids in preventing the needle from inadvertent contact with the wall opposite that of the wall being sutured. The method includes an initial suture to join the structures, inserting the device into the openings of the two structures, placing sutures in the walls adjacent to a depression, optionally rotating the device so one of the depressions is aligned with each suture as it is being placed, removing the device, and tightening the sutures to complete the anastomosis.

13 Claims, 3 Drawing Sheets

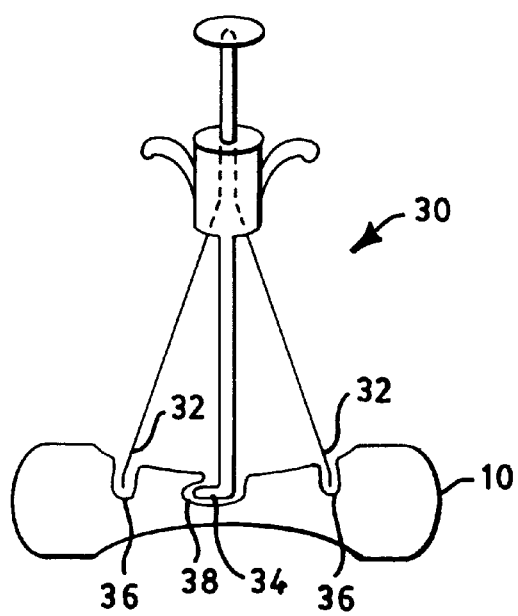
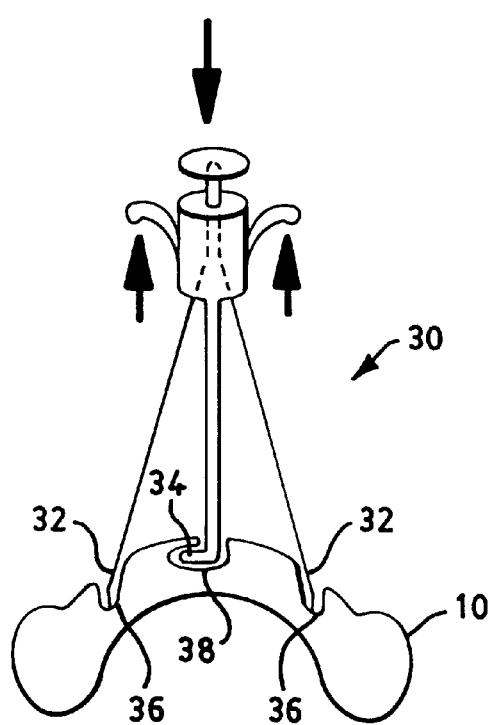
FIG. 17  FIG. 18
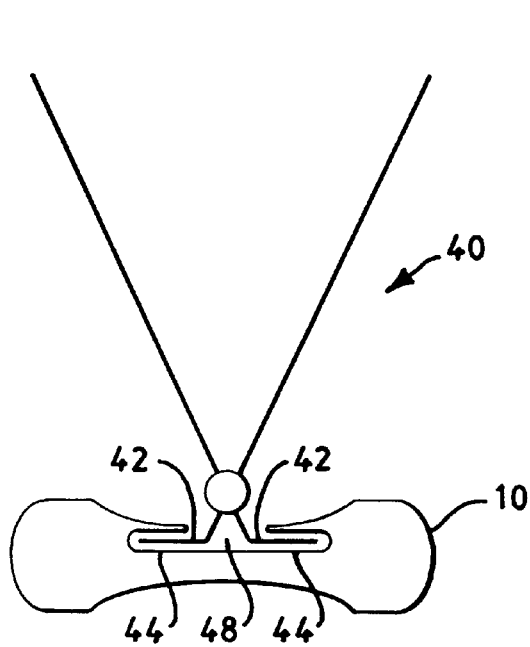
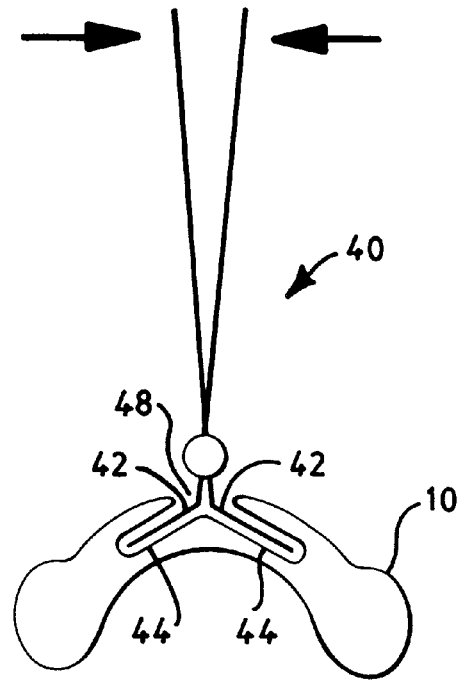
FIG. 19  FIG. 20

DEVICE AND METHOD FOR THE SURGICAL ANASTOMOSIS OF TUBULAR STRUCTURES

BACKGROUND OF THE INVENTION

1. Field of the Invention

The present invention relates to a device and method for surgically joining severed small tubular structures.

2. The Prior Art

It is presently possible to surgically join small tubular structures, for example, severed arteries smaller than 5.0 millimeters (mm) in size, and even less than 1.0 mm in size. However, considerable surgical dexterity is required. If reunification of a patent conduit with normal or nearly normal flow is to be achieved, great pains must be taken to insure gentle handling of delicate tissues, particularly avoiding unnecessary stretching, crushing, or piercing of the tissues. Such trauma increases the likelihood of thrombosis and/or structural failure.

Anastomosis of small tubular structures is preferably performed under a microscope to aid in visualization. In the case of end-to-end anastomosis, the severed vessels are gently clamped so as to interrupt flow and to make the ends available for suture. An initial suture is installed to connect the ends together at a single point. This initial suture is usually positioned at the anatomically deepest aspect of the anastomosis, a position which is generally referred to as the "back wall" or "posterior wall" of the anastomosis. Additional sutures are then placed to join additional points of the separated ends.

A number of factors contribute to the difficulty of performing this procedure:

(a) Loss of Configuration

When tubular structures, such as blood vessels, are emptied of their pressurized contents (such as blood), the tubular lumen collapses and the tubular shape is lost. The ends of such severed, collapsed structures are difficult to visualize in their previously intact configuration or their preferably restored configuration. They are also difficult to grasp and manipulate in order to suture.

(b) Trauma from Instrumentation

In placing sutures through the vessel wall, the suture needle is passed through the wall either from outside to in or from inside to out. To facilitate passing a suture needle inward towards the lumen, an instrument, such as a small forceps, is typically inserted into the lumen in order to provide counter pressure to the thrust of the suturing needle, as well as to attempt to separate the wall being sutured from the wall behind it. Alternatively, the surgeon may be required to grasp the full thickness of the wall being sutured with a forceps in order to position it so that it may be pierced by the suturing needle. This requirement for forceps to grasp and manipulate the dissociated structures introduces an unwanted element of tissue trauma.

(c) Inadvertent Misplacement of Sutures

With tubular shapes, especially those of small diameter, the opposite wall from the point being sutured might be inadvertently pierced or traversed in the line of the thrust of the suturing needle, especially in placing sutures through the vessel wall from outside to in, toward the lumen. This is especially so because of the lumen being collapsed. Not only might tissues of the opposing wall be traumatized, but the lumen may be inadvertently sutured shut.

(d) Spasm of the Vessel

Trauma to the vessel may cause it to spasm, adding a complicating factor in performing these procedures.

(e) Time for Performance

The present methods of performing anastomoses are time consuming. Surgical risk, particularly anesthetic risk, is known to be increased with time.

(f) Operator Fatigue

The intense concentration, effort and time required by the present methods contribute to frustration and fatigue.

SUMMARY OF THE INVENTION

An object of the present invention is to provide a device and method for surgically joining severed small tubular structures that minimizes the problems associated with methods of the prior art. It renders the process less technically demanding, decreases tissue trauma associated with grasping and manipulating tissues, diminishes the occurrence of inadvertent piercing trauma in the line of suture needle thrust, facilitates speed, and decreases operator fatigue.

The basic device of the present invention is described in detail in U.S. Pat. No. 5,868,765 (the '765 patent), incorporated herein by reference. The device of the present invention differs from the '765 device by having two or more depressions, i.e., the device has a generally cylindrical shape that includes a pair of insertion arms and two or more depressions that provide space for the needle to move within the lumen of the tubular structures. The depressions leave a bridge connecting the arms. The arms have free extremities for inserting the device into the tubular structure. The area of the juncture of each depression with the outermost cylindrical surface of the device may provide support so that the needle thrust does not collapse the wall. Any two depressions may be either separate or overlapping. The configuration of the bridge is generally determined by the configuration of the depressions.

A function of the device is to aid in preventing needle contact with the opposite wall of the tubular structure. This is done in one or both of two ways. One way is as described in the '765 patent: the bridge acts as a guard to physically prevent the needle from contacting the opposite wall. In the second, the insertion arms of the inserted device restore the structure of the otherwise collapsed walls of the tubular structures, thereby separating the walls, and the narrowed bridge provides visibility within the structure so that the user can see to avoid inadvertent contact of the wall by the needle.

Optionally, the device includes a means for being inserted and removed and/or manually rotated while residing in the tubular structure. Several such methods are described in the '765 patent. Another means uses a tool with arms that grasp the device at complementary radial notches within the device. Another means uses a tool with feet that fit within complementary axial notches within the device. When the tool is closed, the device bends at the resilient bridge for easy insertion or removal.

The method of the present invention is much the same as that of the method of the '765 patent, the difference being that a larger number of depressions means that the device does not have to be rotated as frequently.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein:

FIG. 17 is a side cross-sectional view of a configuration of the device and a tool for grasping the device;

FIG. 18 is a side cross-sectional view of the configuration of FIG. 17 with the tool flexing the device;

FIG. 19 is a side cross-sectional view of a configuration of the device and another tool for grasping the device; and FIG. 20 is a side cross-sectional view of the configuration of FIG. 19 with the tool flexing the device.

DETAILED DESCRIPTION

Figure 1:
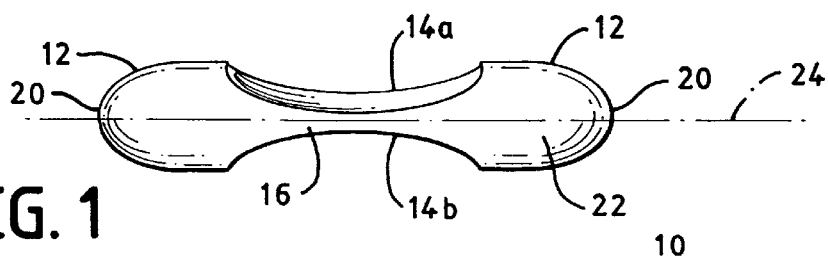
FIG. 1 is a perspective view of a device of the present invention with two separate depressions.

The basic device of the present invention is described in detail in U.S. Pat. No. 5,868,765 (the '765 patent), incorporated herein by reference. That device has a generally cylindrical shape and includes a pair of insertion arms and a single central depression. The depression leaves a bridge connecting the arms.

Several embodiments and configurations of the device 10 of the present invention are shown in FIGS. 1–16. These devices have a generally cylindrical shape, and includes a pair of insertion arms 12 and two or more depressions 14. The depressions 14 leave a bridge 16 connecting the arms 12.

The insertion arms 12 are designed to be non-traumatic when in contact with the inside of the tubular structure. This may be accomplished by either making the outer surface of the arms 12 smooth, by forming the arms 12 of a material that retains moisture, and/or by coating the arms 12 with a lubricant. As an aid to insertion, the free extremities 20 of the arms 12 are convexly rounded. Optionally, the free extremities are tapered. A tapered extremity may be easier to insert because the tubular structure, which is collapsed when empty, does not have to be opened as far to start the insertion process.

The arms 12 may have the same or different lengths and/or the same or different cross-sections, as may be needed for particular applications. The cross-sectional area is approximately that of the tubular structure so that it will support the structure without stretching it. The cross-section may be round, oval, or such other desired shape. The arms 12 are preferably constructed of relatively firm material. Preferably, the arms 12 are constructed of a biologically compatible material.

The device 10 of the present invention differs from the device of the '765 patent by the number of depressions 14. The depression 14 permits the suture needle room to move through the wall when passing from outside to inside, and allows space for the suture needle positioned inside the wall to be passed outwardly through the wall. The depth, length, and width of the depression 14 may vary depending upon the application. The depression 14 may be configured and positioned so that its edge 18 places counter pressure on the inside of the tubular structure wall so as to oppose the thrust of the suture needle when passed from outside to in. The depression 14 may be configured to guide the placing of sutures and/or limit the path of the suture needle.

The '765 device has a single depression on one side of the device. The present device 10 has two or more depressions 14 in a theoretically infinite number of configurations. A depression 14, as shown in FIG. 1, is defined as a curved indentation taken from the side 22 of the device 10. The bottom of the depression 22 may be straight, as in FIG. 3, or concave, as in FIG. 5.

Figure 2:
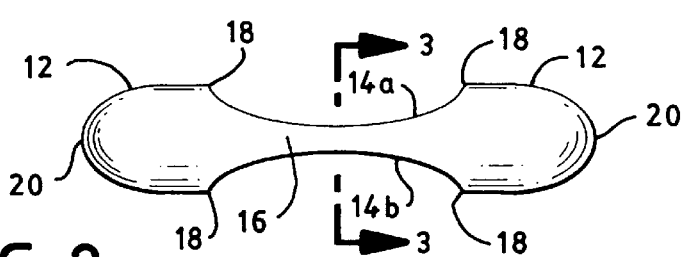
FIG. 2 is a side view of the device of FIG. 1.
Figure 3:
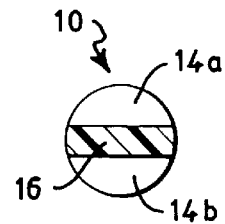
FIG. 3 is a cross-sectional view of the device of FIG. 1 taken along the line 3—3.
Figure 4:
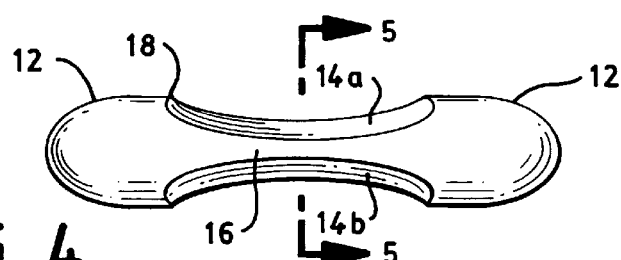
FIG. 4 is a side view of the device of the present invention with three separate depressions.
Figure 5:
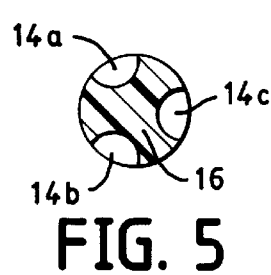
FIG. 5 is a cross-sectional view of the device of FIG. 4 taken along the line 5—5.
Figure 6:
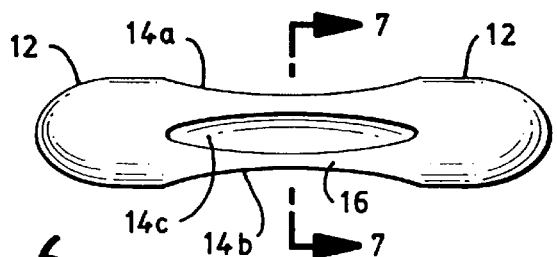
FIG. 6 is a side view of the device of the present invention with four separate depressions.
Figure 7:
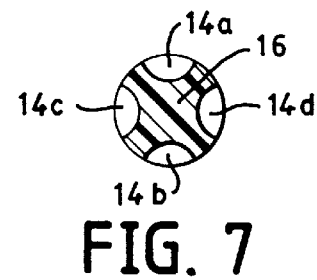
FIG. 7 is a cross-sectional view of the device of FIG. 6 taken along the line 7—7.
Figure 8:
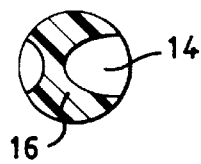
FIG. 8 is a cross-sectional view of another example device of the present invention.
Figure 9:
FIG. 9 is a cross-sectional view of another example device of the present invention.

The most basic configuration of the device of the present invention is shown in FIGS. 1–3, and includes a pair of depressions 14a, 14b on opposite sides of the device 10. In the configuration of FIGS. 4 and 5, there are three depressions 14a–c spaced around the circumference of the device 10. In the configuration of FIGS. 6 and 7, there are four depressions 14a–d, where opposed pairs 14a, 14b and 14c, 14d are of equal size. The present invention contemplates that any number of depressions 14 can be located along the circumference of the device 10. It is not necessary that the depressions 14 be located symmetrically about the circumference. It is also contemplated that the various depressions 14 may be of different sizes and shapes, as the examples of FIGS. 8 and 9 show.

Figure 10:
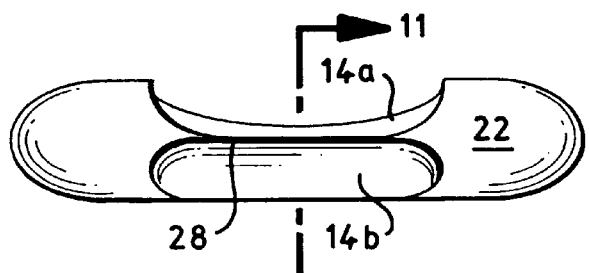
FIG. 10 is a perspective view of a two depression device where the depressions overlap.
Figure 11:
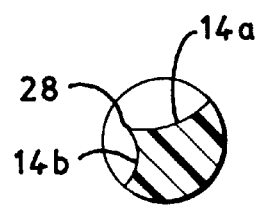
FIG. 11 is a cross-sectional view of the device of FIG. 11 taken along the line 11—11.
Figure 12:
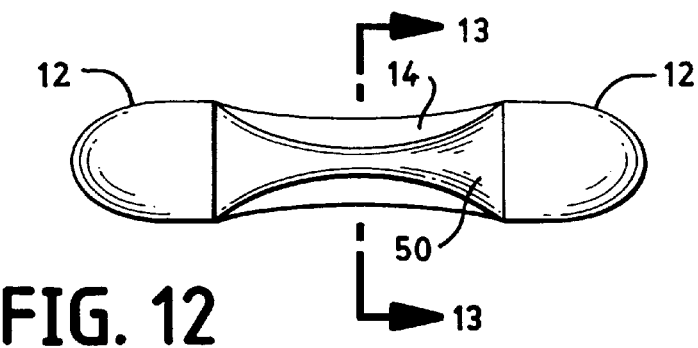
FIG. 12 is a side view of one configuration of an infinite series of depressions.
Figure 13:
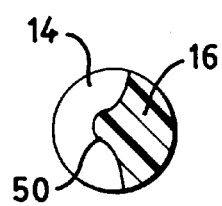
FIG. 13 is a cross-sectional view of the configuration of FIG. 12 taken along the line 13—13.
Figure 14:
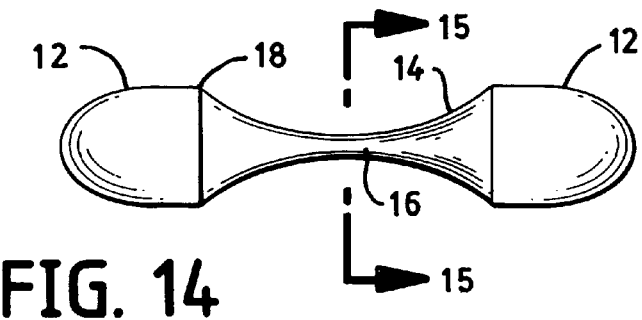
FIG. 14 is a side view of another configuration of an infinite series of depressions.
Figure 15:
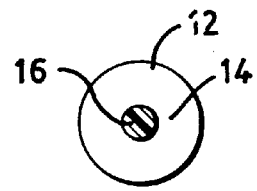
FIG. 15 is a cross-sectional view of the configuration of FIG. 14 taken along the line 15—15.

The present invention also contemplates that the depressions 14 may overlap each other, as in the simple example of FIGS. 10 and 11. The overlap leaves an edge 28 at the intersection of the depressions 14a, 14b. If an infinite number of depressions 14 extends completely around the device 10, an annular narrowing results, as in FIGS. 14 and 15. The present invention contemplates that the series of depressions may extend around the device for any angle. In the examples of FIGS. 12 and 13 and FIGS. 14 and 15, the angles are approximately 180° and 360°, respectively.

A function of the device 10 is to aid in preventing needle contact with the wall of the tubular structure opposite that of the wall being sutured. It accomplishes this in one or both of two ways, depending upon the size and shape of the bridge 16. One way is as described in the '765 patent: When the suture needle passes into the depression 14, the bridge 16 acts as a guard to prevent the needle from contacting the opposite wall. Accordingly, the bridge material, in addition to its preferred flexibility, is preferably made of a material and in a thickness which is difficult for the suture needle to penetrate. The configurations of FIGS. 1–13 employ this manner of preventing needle contact. The main reason is that the bridge 16 extends completely or nearly completely across the diameter of the tubular structure.

Figure 16:
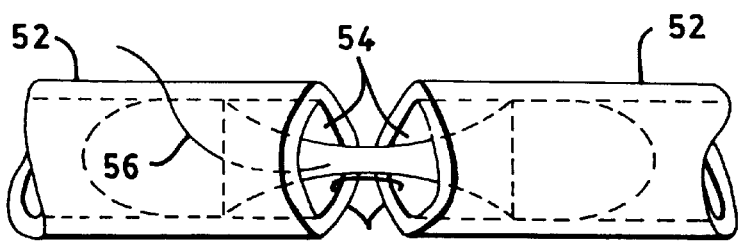
FIG. 16 is a top, phantom view of how the present invention improves visibility to the opposite wall of the tubular structures.

The second way in which the device 10 helps prevent needle contact with the opposite wall is by providing the user with visibility so that the user can avoid contact with the opposite wall. As indicated above, when the device of the present invention is not used, the tubular structures are collapsed because there is no internal pressure. When in place, the insertions arms 12 open up the interior of the tubular structures. When employing configurations like that of FIGS. 14 and 15, where the bridge 14 does not extend completely across the diameter of the tubular structure, visibility to the opposite wall is provided. An example is seen in FIG. 16. The device 10 opens the tubular structures 52 so that the wall 54 opposite the point where the needle 56 is inserted is visible.

Optionally, the device 10 includes a means for being inserted, removed and/or manually rotated while residing in the tubular structure. Several such methods are described in the '765 patent and are also contemplated for use in the present invention.

Another method is illustrated in FIGS. 17 and 18, and includes a tool 30 with two tips 32, a foot 34, and a set of complementary notches 36, 38 in the device 10. The tool 30 grasps the device 10 by fitting the tips 32 and foot 34 into their respective notches 36, 38. When the tool 30 is closed, as in FIG. 18, the resilient nature of the bridge 16 causes the device 10 to bend, for easy insertion and/or removal. The present invention contemplates that there may be more than one set of notches 36, 38 around the device 10 so that the user does not have to hunt for the notches 36, 38 when wishing to remove the device 10. Optionally, the device 10 is prepackaged with the tool 30 already grasping the device 10.

Yet another method is illustrated in FIGS. 19 and 20, and includes a tool 40 with feet 42, a pair of complementary axial notches 44 in the device 10, and an opening 48 to allow access to the notches 44 by the tool 40. The tool 40 grasps the device 10 by fitting the feet 42 into the notches 44. When the tool 40 is closed, the resilient nature of the bridge 16 causes the device 10 to bend, as in FIG. 21, for easy insertion and/or removal. Optionally, the device 10 is prepackaged with the tool 40 already grasping the device 10.

The method of the present invention is essentially the same as the method described in the '765 patent, with a difference attributable to the different number and/or shape of the depressions 14. A larger number of depressions means that the device may not have to be rotated after most every suture, as in the method of the '765 patent.

Thus it has been shown and described a device and method for surgically joining tubular structures which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A device to aid in surgically joining a pair of tubular structures at openings thereof, said device comprising:
   (a) a generally cylindrical body having an axis, a pair of opposed arms, a bridge between said arms, and at least two depressions between said arms;
   (b) said arms having free extremities that are adapted for insertion into said tubular structure openings;
   (c) said depressions being adapted to allow a suturing needle to pass through a wall of each of said tubular structures; and
   (d) said device being adapted to aid in preventing trauma to said wall from said needle opposite where said needle passes through said wall.

2. The device of claim 1 wherein there is no overlap between said depressions.

3. The device of claim 1 wherein at least two of said depressions overlap.

4. The device of claim 1 wherein said bridge aids in preventing trauma to said opposite wall from said needle by being interposed between said needle and said opposite wall.

5. The device of claim 1 wherein said bridge aids in preventing trauma to said opposite wall from said needle by providing visibility to said opposite wall for a user.

6. The device of claim 1 wherein said device includes a structure for grasping.

7. The device of claim 1 wherein said bridge is flexible and said device includes a structure for grasping and flexing said device.

8. A method for surgically joining a pair of tubular structures at openings thereof, said method comprising the steps of:
   (a) providing a device with a generally cylindrical body having a pair of opposed arms, a bridge between said arms, and at least two depressions between said arms, said arms having free extremities that are adapted for insertion into said tubular structure openings, said depressions being adapted to allow a suturing needle to pass through a wall of each of said tubular structures, and said device being adapted to aid in preventing trauma to said wall from said needle opposite where said needle passes through said wall;
   (b) placing a single suture at said tubular structure openings to hold said tubular structures together at a single point;
   (c) inserting said device arm extremities into said tubular structure openings;
   (d) positioning said device in a working position such that at least one of said depressions straddles said tubular structure openings;
   (e) introducing sutures into said tubular structure walls at suture positions adjacent to said depressions for permitting the suturing needle to traverse through said walls;
   (f) removing said device; and
   (g) tightening said sutures.

9. The method of claim 8 wherein inserting and positioning said device includes inserting said device substantially fully into a first of said tubular structures, aligning said openings, and sliding said device into a second of said tubular structures until said device is in said working position.

10. The method of claim 8 wherein inserting said device includes the use of a grasping tool.

11. The method of claim 8 wherein said bridge is flexible and removing said device includes bending said device at said bridge such that said bridge extends outwardly through said sutures.

12. The method of claim 8 wherein removing said device includes the use of a grasping tool.

13. The method of claim 8 wherein said bridge is flexible and removing said device includes the use of a tool that grasps and flexes said device.

* * * * *